(12) United States Patent
Chen et al.

(10) Patent No.: US 8,985,056 B2
(45) Date of Patent: Mar. 24, 2015

(54) DETECTING PLATFORM FOR HOLDING A TINY INSECT

(75) Inventors: Rong-Shun Chen, Hsinchu (TW);
Jhih-Shun Yang, Hsinchu (TW);
Yu-Ching Lin, Hsinchu (TW);
Hung-Yin Tsai, Hsinchu (TW);
Chien-Hung Lin, Hsinchu (TW); Hong Hocheng, Hsinchu (TW); Li-An Chu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 147 days.

(21) Appl. No.: 13/419,090

(22) Filed: Mar. 13, 2012

(65) Prior Publication Data

US 2013/0081572 A1 Apr. 4, 2013

(30) Foreign Application Priority Data

Sep. 29, 2011 (TW) .............................. 100135299 A

(51) Int. Cl.
*A01K 1/03* (2006.01)
*A01K 67/033* (2006.01)
(52) U.S. Cl.
CPC .................................... *A01K 67/033* (2013.01)
USPC ............................ 119/417; 119/6.5; 119/421
(58) Field of Classification Search
USPC ....................... 119/6.5, 417, 421; 43/107, 121
See application file for complete search history.

(56) References Cited

U.S. PATENT DOCUMENTS

| 554,616 | A | * | 2/1896 | Cook ............................... 43/121 |
| 3,580,219 | A | * | 5/1971 | Stebbins ........................ 119/6.5 |
| 3,789,799 | A | * | 2/1974 | Orfei .............................. 119/6.5 |
| 3,874,335 | A | * | 4/1975 | Galasso ......................... 119/6.5 |
| 3,908,302 | A | * | 9/1975 | Carr ................................ 43/121 |
| D255,946 | S | * | 7/1980 | Galbreath .................... D30/108 |
| 4,212,267 | A | | 7/1980 | Patterson |
| 4,252,080 | A | * | 2/1981 | Gioia et al. .................... 119/6.5 |

(Continued)

FOREIGN PATENT DOCUMENTS

| CN | 1065726 | 10/1992 |
| CN | 2786629 | 6/2006 |

(Continued)

OTHER PUBLICATIONS

English Translation of the Abstract for CN 2894271 published May 2, 2007.
English Translation of the Abstract for CN 101546094 published Sep. 30, 2009.
English Translation of the Abstract for CN 201252774 published Jun. 10, 2009.

(Continued)

*Primary Examiner* — Monica Williams
*Assistant Examiner* — Michael A Fabula
(74) *Attorney, Agent, or Firm* — Thomas | Horstemeyer, LLP

(57) ABSTRACT

A detecting platform for holding a tiny insect includes a main body forming a containing space, which passes through the main body and is surrounded by side walls of the main body. A first side wall and a second side wall of the side walls are opposite to each other, and the area of the second side wall is smaller than that of the first side wall. The main body forms a first opening and a second opening passing through the first side wall and the second side wall respectively for the tiny insects entering and leaving the containing space. A bottom plate covers a first through surface of the containing space to form a bottom surface and a detecting area is configured thereon to holding the tiny insects. Accordingly, the tiny insects can stay on the detecting area so as to detect the characteristics of the tiny insects expediently.

7 Claims, 2 Drawing Sheets

(56) References Cited

U.S. PATENT DOCUMENTS

| | | | |
|---|---|---|---|
| 5,148,625 A * | 9/1992 | Saleman | 43/121 |
| 5,305,495 A * | 4/1994 | Nelsen et al. | 15/414 |
| 5,646,404 A * | 7/1997 | Litzkow et al. | 250/338.1 |
| 5,907,923 A * | 6/1999 | Heath et al. | 43/122 |
| 5,930,944 A * | 8/1999 | Knuppel | 43/114 |
| 6,338,315 B1 * | 1/2002 | Stillman | 119/51.01 |
| D483,834 S * | 12/2003 | Shultz | D22/122 |
| D566,147 S * | 4/2008 | Chan | D16/131 |
| 8,375,624 B2 * | 2/2013 | Blazer et al. | 43/107 |
| 8,667,731 B2 * | 3/2014 | Panella et al. | 43/139 |
| 2006/0283075 A1 * | 12/2006 | Feldhege et al. | 43/114 |
| 2007/0169403 A1 * | 7/2007 | Collins | 43/139 |
| 2011/0132278 A1 | 6/2011 | Robinson, Jr. | |

FOREIGN PATENT DOCUMENTS

| | | |
|---|---|---|
| CN | 2894271 | 5/2007 |
| CN | 201252774 | 6/2009 |
| CN | 101546094 | 9/2009 |
| CN | 101701906 | 5/2010 |

OTHER PUBLICATIONS

English Translation of the Abstract for CN 101701906 published May 5, 2010.

English Translation of the Abstract for CN 1065726 published Oct. 28, 1992.

English Translation of the Abstract for CN 2786629 published Jun. 7, 2006.

* cited by examiner

DETECTING PLATFORM FOR HOLDING A TINY INSECT

CROSS-REFERENCE TO RELATED APPLICATION

This application claims priority to and the benefit of Taiwan Application Serial Number 100135299 filed on Sep. 29, 2011, which is incorporated by reference in its entirety.

BACKGROUND OF THE INVENTION

1. Field of the Invention

The present invention relates to a detecting platform for holding a tiny insect, and more particularly, to a detecting platform which can confine a tiny insect in the detecting area so as to detect the characteristics of the insect expediently.

2. Description of the Prior Art

Genetics is the science of genes, heredity, and variation in living organisms, and meanwhile genetics is an important branch of life science. For other branches, many of them are derived from the research of gene based on genetics, such as genetic engineering. Genetics not only plays a large role in the appearance and behavior of organisms but also can explain the macroscopic property of biological phenomenon with microscopic analysis. With the development and prosperity of genetic, the physiological problem, such as aging and disease, has been improved. Therefore, many researchers pay attention to the research of genes.

The genetic number of fruit flies is about one third of the number of human genes, however, the controlling gene of fruit flies is similar to the controlling gene of humanity in physical development, additionally, with the advantages of the short life cycle and mass reproduction, fruit flies became a popular model organism in genetics research. So far, there are a lot of research about fruit flies in genetics, cell-biology, biochemistry, and especially developmental biology. Fruit flies made a greater contribution to genetics knowledge for almost a century.

In the genetic research of fruit flies, the researchers need to collect unbred female fruit flies, in order to confirm that the result of the genetics experimentation is accurate without any influence of male genes. To recognize unbred female fruit flies, the fruit fly should be fixed below the microscopy manually and then distinguish the abdominal characteristic in conventional method. Due to fruit flies breed abundantly and rapidly, and the female fruit flies take eight hours to turn into sexual maturation after eclosion, it is necessary to keep on doing gender identification between the same interval so as to avoid fruit flies mating with each other. Otherwise, fruit flies are too small to be observed, so the researchers need to spend a large amount of money and time to adjust and improve the position of fruit fly for optimum observation. Therefore, it is really inefficient with the above method.

In addition to fruit flies, other research fields still need to implement with the above method, such as identifying the different insects or recognizing different characteristics of the same breed insect, thus other research fields have the same problem as the conventional method.

SUMMARY OF THE INVENTION

Therefore, a scope of the invention is to provide a new type of detecting platform for holding a tiny insect which can improve the problems of the prior art.

According to an embodiment of the invention, the detecting platform for holding a tiny insect comprises a main body, and the main body forms a containing space, which passes through the main body and is surrounded by a plurality of side walls of the main body. The plurality of side walls comprise a first side wall and a corresponding second side wall. Furthermore, the first side wall and the second side wall of the side walls are opposite to each other, and the area of the second side wall is smaller than that of the first side wall. The detecting platform for holding a tiny insect further comprises a bottom plate, and the bottom plate is removably assembled to the main body and covers a first through surface of the containing space to form a bottom surface, and the bottom surface comprising a detecting area for holding the tiny insect. Accordingly, the tiny insects can stay on the detecting area so as to detect the characteristics of the tiny insects expediently.

In the embodiment of the invention, the detecting platform for holding a tiny insect comprises a first opening which is configured on the main body and interconnected with the containing space through the first side wall, so that the tiny insect can enter the containing space through the first opening. Additionally, the detecting platform for holding a tiny insect further comprises a second opening for the tiny insect leaving the containing space, which is configured on the main body and interconnected with the containing space through the second side wall.

Many other advantages and features of the present invention will be further understood by the detailed description and the accompanying sheet of drawings.

BRIEF DESCRIPTION OF THE APPENDED DRAWINGS

To facilitate understanding, identical reference numerals have been used, where possible to designate identical elements that are common to the figures.

DETAILED DESCRIPTION OF THE INVENTION

Figure 1:
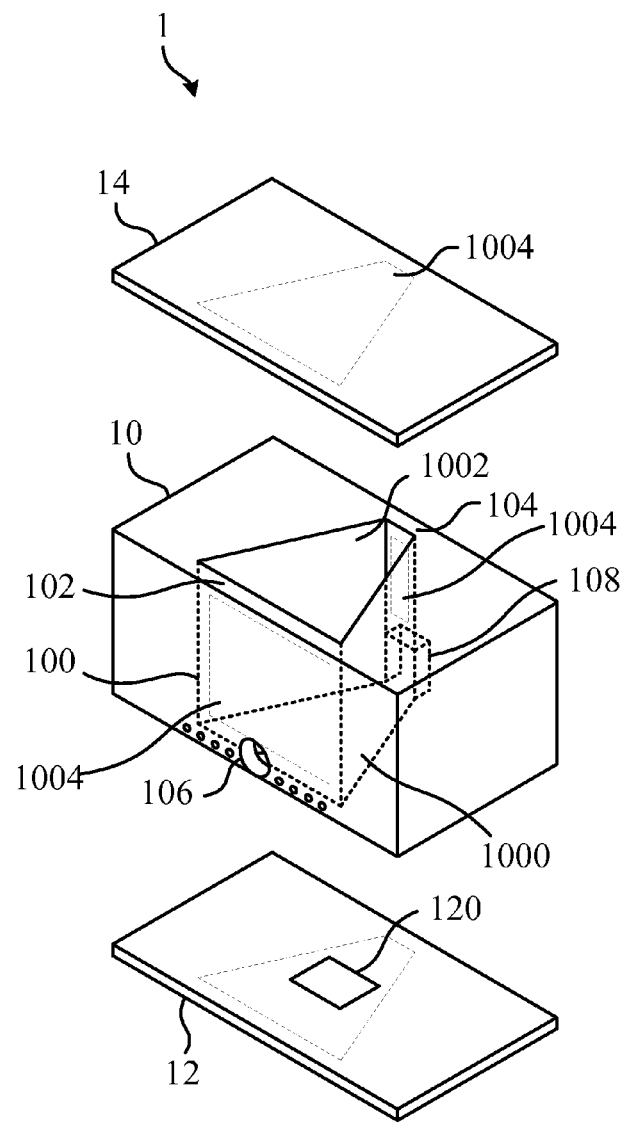
FIG. 1 is a schematic diagram illustrating an embodiment of a detecting platform for holding a tiny insect according the invention.

The invention discloses a detecting platform for holding a tiny insect. More particularly, the invention can improve the problems of the prior art. Please refer to FIG. 1. FIG. 1 is a schematic diagram illustrating an embodiment of a detecting platform for holding a tiny insect according the invention. As shown in FIG. 1, the detecting platform for holding a tiny insect 1 comprises a main body 10 and a bottom plate 12, wherein the bottom plate 12 is removably assembled to the main body 10.

In the embodiment, the main body 10 forms a containing space 100. To elaborate further, the main body 10 has a plurality of side walls, and these side walls surround the containing space 100 so as to define the shape of the containing space 100. Moreover, the containing space 100 passes through the main body 10, and forms upper and lower through surfaces on the surface of the main body 10.

The plurality of side walls surrounding the containing space 100 comprise a first side wall 102 and a second side wall 104, wherein the area of the second side wall 104 is smaller than the area of the first side wall 102, therefore the containing space 100 is a convergent structure. In the embodiment, the cross-section of the containing space 100 is a trapezoid.

Additionally, the main body 10 comprises a first opening 106 and a second opening 108, wherein the first opening 106 is configured on the first side wall 102 of the main body 10 and interconnected with the large side of the containing space 100 through the first side wall 102; the second opening 108 is configured on the main body 10 and interconnected with another small side of the containing space 100 through the second side wall 104. And hence, the tiny insect can enter or leave the containing space 100 through the first opening 106 and the second opening 108.

A bottom plate 12 is removably assembled to the main body 10 and covers a first through surface 1000 of the containing space 100 to form a bottom surface. When the tiny insect enter the containing space 100 through the first opening 106, the tiny insect can stay on the bottom surface. Moreover, the detecting platform for holding a tiny insect 1 further comprises an upper cover plate 14 which is removably assembled to the main body 10 and covers a second through surface 1002 of the containing space 100 to form an upper wall. The upper wall can cover the approach of the containing space 100, so as to avoid the tiny insect leaving the containing space 100 through the second through surface 1002.

In actual application, the bottom plate 12 comprises a detecting area 120 on the bottom surface of the containing space 100. A detector for tiny insect can detect the characteristics of tiny insect within the detecting area 120. However, it is difficult to detect the moving insect in the containing space 100, so that confining the tiny insect in the detecting area 120 is helpful.

In the embodiment, the side walls of the main body 10 including the first side wall 102 and the second side wall 104 further comprise a repellent, such as FULON, Ethylene Tetrafluoroethylene (ETFE). The repellent is a coating material 1004 which can prevent the tiny insect staying on the side walls and limit the actions of the tiny insect. Otherwise, the upper wall is also coated with the coating material 1004 mentioned above, and hence the tiny insect cannot stay on the upper wall. Therefore, the tiny insect is confined on the bottom surface of the containing space 100, and it is beneficial to detect the characteristics of tiny insect expediently.

According to another embodiment, the detecting platform for holding a tiny insect 1 comprises a restriction mechanism which is configured on the containing space to confine the tiny insect in the detecting area 120. In actual application, the restriction mechanism can be a punishment system.

Additionally, the bottom plate 12 is a transparent plate in the embodiment, and a detector can be operated below the bottom plate 12 to detect the detecting area 120. In other words, the detector which can photograph is operated below the bottom plate 12 of the detecting platform for holding a tiny insect 1, and the researcher can observe the characteristics of the tiny insect in the detecting area 120 at the same time. For example, in the genetic research of fruit flies, the researchers need to collect unbred female fruit flies, in order to confirm that the result of the genetics experimentation is accurate without any influence of male genes. Due to the abdominal characteristics of unbred female fruit flies differ from the others, the researchers can identify the gender of the fruit flies. Therefore, the detecting platform for holding a tiny insect 1 provides an approach to the containing space 100 of the main body 10 for the fruit fly. The fruit fly can be confined in the detecting area 120 with abdomen down towards the bottom plate 12, and then a detector can be operated below the bottom plate 12 to detect the abdominal characteristic of fruit fly.

In the embodiment, the detecting area 120 is a square, so that can decrease the effect of reflected-light. In actual application, the shape of the detecting area can be adjusted according to the needs of the user. For example, to improve the problem of reflected-light, the shape of the detecting area can be designed depending on the diverse shapes of the containing space. Otherwise, a suitable detecting area can be designed depending on the diverse detection methods, such as voice or scent recognition for insects.

Figure 2:
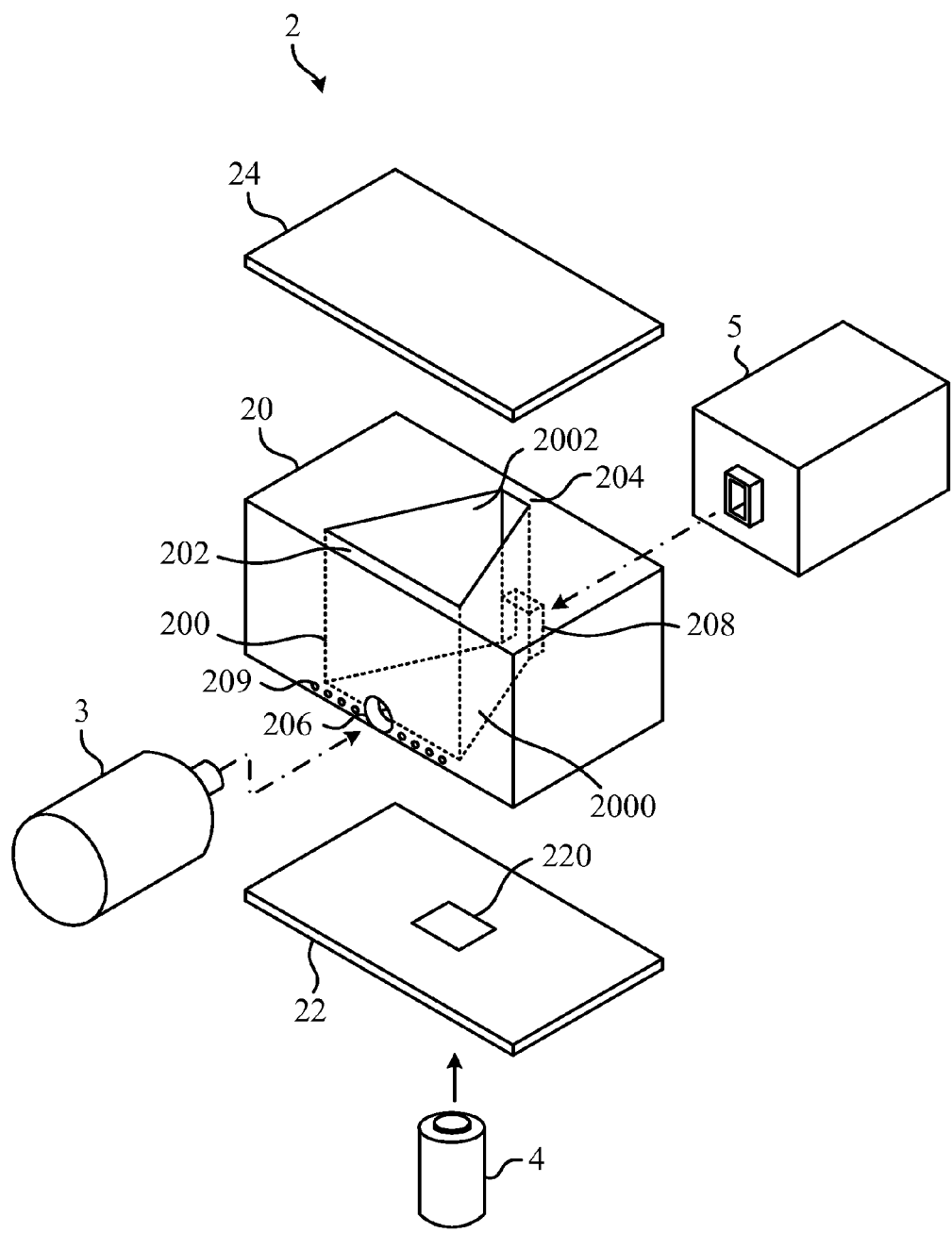
FIG. 2 is a schematic diagram illustrating another embodiment of a detecting platform for holding a tiny insect in actual application according to the invention.

Please refer to FIG. 2. FIG. 2 is a schematic diagram illustrating another embodiment of a detecting platform for holding a tiny insect in actual application according to the invention. As shown in FIG. 2, the detecting platform for holding a tiny insect 2 can detect the tiny insect with a culture tank 3, a detector 4, and a gathering unit 5.

As shown in FIG. 2, the detecting platform for holding a tiny insect 1 in the embodiments mentioned previously and the detecting platform for holding a tiny insect 2 in this embodiment are in essence the same, thus the components needn't be elaborate any further. To be noticed, the main body 20 of the detecting platform for holding a tiny insect 2 further comprises a plurality of bleeder holes 209 which are configured on the first side wall 202, and interconnected with the containing space 200 through the first side wall 202. Moreover, each size of the bleeder holes 209 is smaller than the body size of tiny insect, so as to prevent the tiny insect leaving the containing space 200 through the bleeder holes 209.

In the embodiment, the first opening 206 of the main body 20 is connected to the culture tank 3 for storing the tiny insect, and the tiny insect from the culture tank 3 can enter the containing space 200 of the main body 20 through the first opening 206. The detector 4 can be operated below the bottom plate 22 to detect the tiny insect in the containing space 200, and deliver the detection results to the control device, wherein the detection result can be voices, scents, and/or images. After detecting, the tiny insect can leave from the containing space 200 and enter the gathering unit 5 through the second opening 204. In actual application, the size of the first opening 206 can be designed to be a suitable dimension, so as to allow only one tiny insect to pass and avoid too many tiny insects entering the containing space 200 from the culture tank 3 at once, so that the detection result can be accurate.

Furthermore, in order to impel the tiny insect to enter or leave the containing space 200, driving factors or extrinsic incentives are applied on the detecting platform for holding a tiny insect 2. For example, applying light source, scents, and/or magnetic toward the culture tank 3, causes the tiny insect to enter the containing space 200 by the instincts. Additionally, the gathering unit 5 can further comprise a suction device on the second opening 208 for sucking the tiny insect out of the containing space 200. Otherwise, the plurality of bleeder holes 209 can draw in the external air to allow the air to circulate, when the suction device of gathering unit 5 works. Due to the convergent structure of the containing space 200, the tiny insect can be sucked into the gathering unit 5 without hindrances.

According to the above, the invention is to provide a detecting platform for holding a tiny insect, and this detecting platform can confine the tiny insect in the detecting area so as to detect the characteristics of insect expediently. After detecting, the tiny insect can be suck out of the containing space. Wherein, the convergent structure is beneficial to suck the tiny insect out. Compared to the prior art, the invention can detect the characteristics of insect more efficiently and reduce the resource consumption, with the automated control system.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. An insect detecting platform for holding a tiny insect, comprising:
   a main body forming a containing space which passes through the main body and the main body having a plurality of side walls surrounding the containing space, wherein the plurality of side walls comprise a first side wall and an opposing second side wall, and the area of the second side wall is smaller than the area of the first side wall;
   a first opening for the tiny insect entering the containing space, configured on the main body and interconnected with the containing space through the first side wall;
   a plurality of bleeder holes configured on the main body, and interconnected with the containing space through the first side wall;
   a second opening for the tiny insect leaving the containing space, configured on the main body and interconnected with the containing space through the second side wall;
   a gathering unit connected to the second opening, wherein the gathering unit further comprises a suction device for sucking the tiny insect from out of the containing space and into the gathering unit through the second opening; and
   a bottom plate removably assembled to the main body and covering a first through surface of the containing space to form a bottom surface, and the bottom surface comprising a detecting area for holding the tiny insect;
   wherein the bleeder holes draw external air into the containing space so that the air is circulated inside the space and directed towards the gathering unit by the convergent side walls when the suction device is operated.

2. The insect detecting platform for holding a tiny insect of claim 1, further comprising a non-stick coating material on the side walls to limit the actions of the tiny insect.

3. The insect detecting platform for holding a tiny insect of claim 1, further comprising an upper cover plate removably assembled to the main body and covering a second through surface of the containing space to form an upper wall.

4. The insect detecting platform for holding a tiny insect of claim 3, further comprising a non-stick coating material on the upper wall to limit the actions of the tiny insects.

5. The insect detecting platform for holding a tiny insect of claim 1,
   wherein the bottom plate is a transparent plate; and
   further comprising a detector arranged below the bottom plate to detect the tiny insect in the detecting area.

6. The insect detecting platform for holding a tiny insect of claim 1, wherein the detecting area is a square.

7. The insect detecting platform for holding a tiny insect of claim 1,
   wherein the first opening is connected to a culture tank; and
   wherein the tiny insect from the culture tank is capable of entering the containing space through the first opening.

* * * * *